(12) United States Patent
Ravikumar

(10) Patent No.: US 8,133,255 B2
(45) Date of Patent: Mar. 13, 2012

(54) MINIMALLY INVASIVE SURGICAL ASSEMBLY AND METHODS

(75) Inventor: Sundaram Ravikumar, Briarcliff, NY (US)

(73) Assignee: Mini-Lap Technologies, Inc., Dobbs Ferry, NY (US)

( * ) Notice: Subject to any disclaimer, the term of this patent is extended or adjusted under 35 U.S.C. 154(b) by 1160 days.

(21) Appl. No.: 11/655,450

(22) Filed: Jan. 19, 2007

(65) Prior Publication Data

US 2007/0213767 A1    Sep. 13, 2007

Related U.S. Application Data

(63) Continuation-in-part of application No. 11/420,927, filed on May 30, 2006, now Pat. No. 7,766,937.

(60) Provisional application No. 60/781,556, filed on Mar. 13, 2006.

(51) Int. Cl.
*A61B 17/28* (2006.01)
*A61B 17/29* (2006.01)
*A61B 17/295* (2006.01)
*A61B 17/32* (2006.01)

(52) U.S. Cl. ......... 606/206; 606/205; 606/167; 606/185

(58) Field of Classification Search .......... 606/205–207, 606/167, 170, 185, 190, 193, 198; 604/164.01, 604/164.04, 164.12, 106; D24/143
See application file for complete search history.

(56) References Cited

U.S. PATENT DOCUMENTS

| | | | |
|---|---|---|---|
| 3,817,251 A | 6/1974 | Hasson | |
| 3,844,291 A | 10/1974 | Moen | |
| 3,938,527 A | 2/1976 | Rioux et al. | |
| 3,967,625 A * | 7/1976 | Yoon | 128/831 |
| 4,016,881 A | 4/1977 | Rioux et al. | |
| 4,077,412 A | 3/1978 | Moosun | |
| 4,174,715 A * | 11/1979 | Hasson | 606/206 |
| 4,570,642 A | 2/1986 | Kane et al. | |
| D293,470 S | 12/1987 | Adler | |
| 5,073,169 A | 12/1991 | Raiken | |
| 5,100,402 A | 3/1992 | Fan | |
| 5,147,316 A | 9/1992 | Castillenti | |

(Continued)

OTHER PUBLICATIONS

Cauterization, Wikipedia entry, Mar. 14, 2008 (4 pages).

*Primary Examiner* — Amy Lang
(74) *Attorney, Agent, or Firm* — Gordon & Jacobson, PC

(57) ABSTRACT

A minimally invasive surgical assembly includes an outer hollow needle which may be used in puncturing skin to insert and advance the surgical instrument into the body, and a coaxial surgical instrument having a shaft which extends through the outer hollow needle. The outer diameter of the needle may be dimensioned such that a wound formed from the hollow needle puncturing the skin is capable of being closed independent of stitching, and may be approximately 2 mm or smaller. The coaxial surgical instrument includes end effectors at the end of the shaft which are biased to an open position such that when the end effectors of the surgical instrument extend out of the needle they open, and they are closed by relative movement of the needle over them. The assembly preferably includes a first fixing element which is used to fix the relative location of the surgical instrument and the needle. The assembly also preferably includes a second fixing element which moves relative to the needle and is located on the outside thereof and which is used to fix the relative location of the needle to the patient.

15 Claims, 9 Drawing Sheets

U.S. PATENT DOCUMENTS

| | | | |
|---|---|---|---|
| 5,176,643 A | 1/1993 | Kramer et al. | |
| 5,176,697 A | 1/1993 | Hasson et al. | |
| 5,201,742 A | 4/1993 | Hasson | |
| 5,222,973 A | 6/1993 | Sharpe et al. | |
| 5,224,954 A | 7/1993 | Watts et al. | |
| 5,290,276 A | 3/1994 | Sewell, Jr. | |
| 5,330,497 A | 7/1994 | Freitas et al. | |
| 5,342,357 A | 8/1994 | Nardella | |
| 5,353,812 A * | 10/1994 | Chow | 128/898 |
| 5,354,283 A * | 10/1994 | Bark et al. | 604/180 |
| 5,375,588 A | 12/1994 | Yoon | |
| 5,417,697 A | 5/1995 | Wilk et al. | |
| 5,425,357 A | 6/1995 | Moll et al. | |
| 5,439,476 A | 8/1995 | Frantzides | |
| 5,527,264 A | 6/1996 | Moll et al. | |
| 5,556,411 A | 9/1996 | Taoda et al. | |
| 5,578,030 A | 11/1996 | Levin | |
| 5,613,937 A | 3/1997 | Garrison et al. | |
| 5,618,306 A | 4/1997 | Roth et al. | |
| 5,626,597 A | 5/1997 | Urban et al. | |
| 5,634,918 A | 6/1997 | Richards | |
| 5,658,272 A | 8/1997 | Hasson | |
| 5,665,100 A * | 9/1997 | Yoon | 606/170 |
| D388,515 S | 12/1997 | Bookwalter et al. | |
| D389,242 S | 1/1998 | Bookwalter et al. | |
| D389,913 S | 1/1998 | Bookwalter et al. | |
| 5,803,902 A | 9/1998 | Sienkiewicz et al. | |
| 5,813,976 A | 9/1998 | Filipi et al. | |
| 5,823,945 A | 10/1998 | Moll et al. | |
| 5,846,191 A | 12/1998 | Wells et al. | |
| 5,857,999 A | 1/1999 | Quick et al. | |
| 5,871,453 A | 2/1999 | Banik et al. | |
| 5,893,873 A | 4/1999 | Rader et al. | |
| 5,906,620 A | 5/1999 | Nakao et al. | |
| 5,919,163 A | 7/1999 | Glickman | |
| 5,951,488 A | 9/1999 | Slater et al. | |
| 5,951,574 A | 9/1999 | Stefanchik et al. | |
| D426,883 S | 6/2000 | Berman et al. | |
| 6,090,042 A | 7/2000 | Rullo et al. | |
| 6,099,550 A | 8/2000 | Yoon | |
| 6,155,439 A | 12/2000 | Draughn | |
| 6,165,184 A | 12/2000 | Verdura et al. | |
| 6,190,311 B1 | 2/2001 | Glines et al. | |
| 6,197,002 B1 | 3/2001 | Peterson | |
| 6,200,263 B1 | 3/2001 | Person | |
| 6,248,062 B1 | 6/2001 | Adler et al. | |
| 6,258,107 B1 | 7/2001 | Balazs et al. | |
| 6,319,266 B1 | 11/2001 | Stellon et al. | |
| 6,322,578 B1 | 11/2001 | Houle et al. | |
| 6,391,046 B1 | 5/2002 | Overaker et al. | |
| 6,428,503 B1 | 8/2002 | Kierce | |
| 6,504,985 B2 | 1/2003 | Parker et al. | |
| 6,610,009 B2 | 8/2003 | Person | |
| 6,616,683 B1 | 9/2003 | Toth et al. | |
| 6,630,103 B2 | 10/2003 | Martin et al. | |
| 6,648,839 B2 | 11/2003 | Manna et al. | |
| 6,736,814 B2 | 5/2004 | Manna et al. | |
| 6,743,237 B2 | 6/2004 | Dhinsda | |
| 6,761,718 B2 | 7/2004 | Madsen | |
| 6,830,578 B2 | 12/2004 | O'Heeron et al. | |
| 6,832,984 B2 | 12/2004 | Stelzer et al. | |
| 6,860,894 B1 | 3/2005 | Pittman | |
| 6,902,536 B2 | 6/2005 | Manna et al. | |
| 6,908,454 B2 | 6/2005 | McFarlane | |
| 6,945,984 B2 | 9/2005 | Arumi et al. | |
| 6,989,003 B2 | 1/2006 | Wing et al. | |
| 7,001,333 B2 | 2/2006 | Hamel et al. | |
| 7,041,055 B2 | 5/2006 | Young et al. | |
| 7,066,879 B2 | 6/2006 | Fowler et al. | |
| 7,112,172 B2 | 9/2006 | Orban, III et al. | |
| 7,169,156 B2 * | 1/2007 | Hart | 606/144 |
| 7,223,267 B2 | 5/2007 | Isola et al. | |
| 2001/0056286 A1 | 12/2001 | Etter et al. | |
| 2003/0040773 A1 | 2/2003 | Arumi et al. | |
| 2003/0130693 A1* | 7/2003 | Levin et al. | 606/205 |
| 2003/0145865 A1 | 8/2003 | Sterman et al. | |
| 2003/0233092 A1* | 12/2003 | Kortenbach et al. | 606/50 |
| 2005/0113737 A1 | 5/2005 | Ashby et al. | |
| 2005/0273133 A1 | 12/2005 | Shluzas et al. | |
| 2007/0250112 A1* | 10/2007 | Ravikumar et al. | 606/205 |
| 2007/0282170 A1* | 12/2007 | Ravikumar | 600/211 |

* cited by examiner

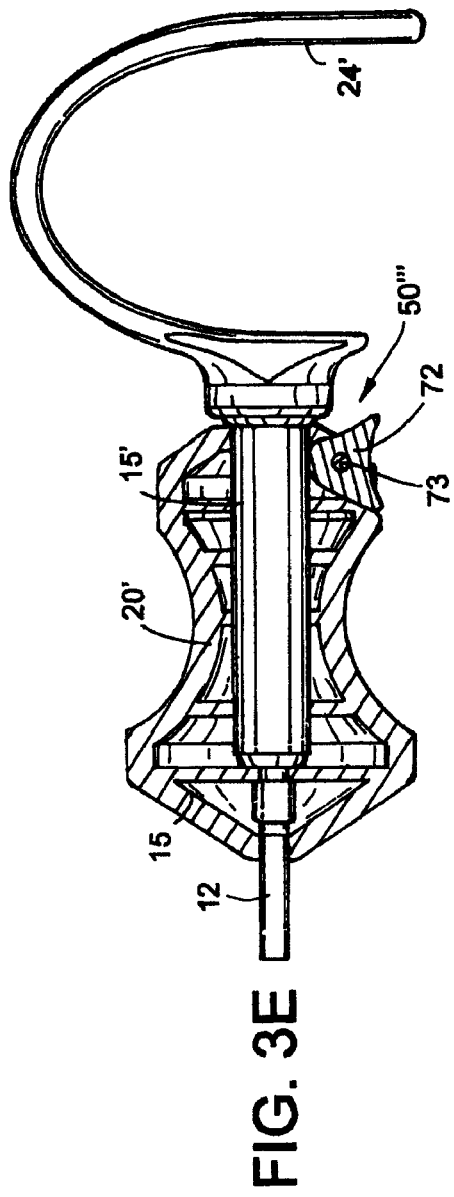
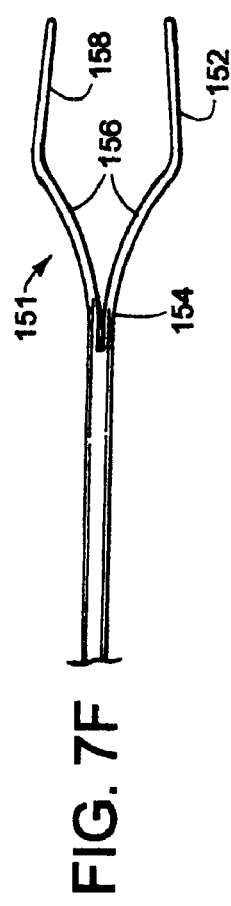
FIG. 3E
FIG. 7F
FIG. 7G

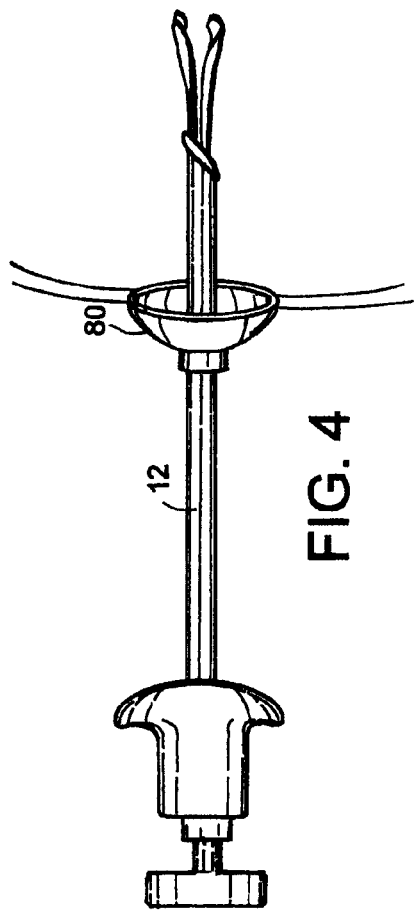
FIG. 4
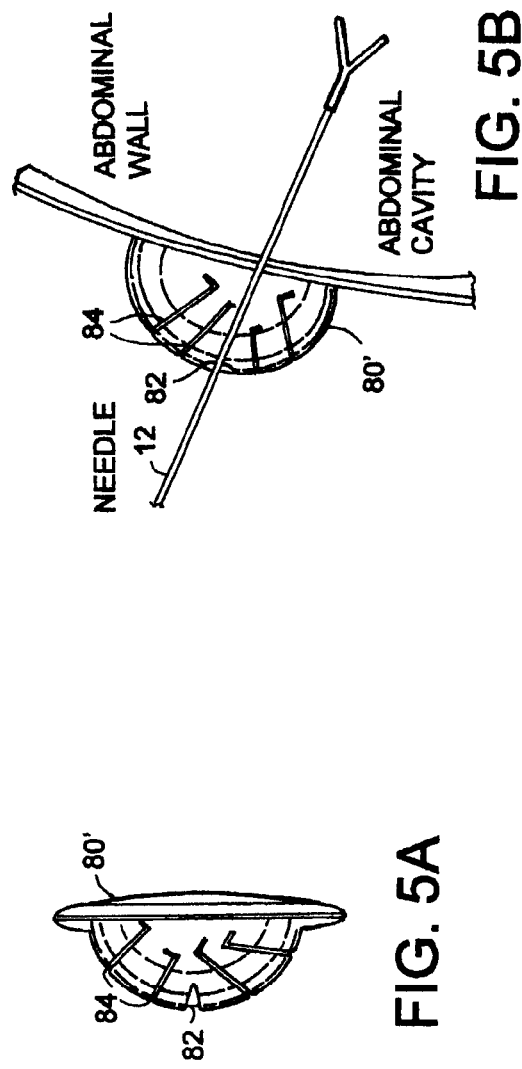
FIG. 5A
FIG. 5B

MINIMALLY INVASIVE SURGICAL ASSEMBLY AND METHODS

This application is a continuation-in-part of U.S. Ser. No. 11/420,927, filed May 30, 2006, now issued as U.S. Pat. No. 7,766,937, which claims the benefit of U.S. Provisional Application No. 60/781,556, filed Mar. 13, 2006, each of which is incorporated by reference herein in its entirety.

BACKGROUND OF THE INVENTION

1. Field of the Invention

This invention relates broadly to surgical instruments and methods of their use. More particularly, this invention relates minimally invasive surgical instruments incorporating a needle and a working device which extends through and beyond the needle and which can be retracted into the needle. The invention has particular application to laparoscopic-type surgery, although it is not limited thereto.

2. State of the Art

Over the last two decades, minimally invasive surgery has become the standard for many types of surgeries which were previously accomplished through open surgery. Minimally invasive surgery generally involves introducing an optical element (e.g., laparoscope or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly. The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm and 12 mm (available from companies such as Taut and U.S. Surgical), which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movements of instruments inside the abdominal cavity to a great extent.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures recognize that even the 5 mm trocar ports leave holes which must be stitched and which result in scars.

A second area of trauma associated with laparoscopic surgery identified by the inventor hereof as being susceptible of reduction relates to trauma resulting from the manipulation (angling) of the trocar ports required in order to conduct the surgery due to inexact placement. Angling of the port can cause tearing at the incision periphery.

Those skilled in the art will also appreciate that because of the number of trocar assemblies and laparoscopic tools used in laparoscopic surgery (most of which are disposable because of the cost and complications associated with autoclaving), the cost of laparoscopic surgery is high. Thus, there always remains a desire in the art to provide lower cost laparoscopic tools.

SUMMARY OF THE INVENTION

It is therefore an object of the invention to provide a minimally invasive surgical assembly which reduces trauma to the patient relative to presently used systems.

It is another object of the invention to provide a minimally invasive surgical assembly which is simple and inexpensive relative to presently used systems.

It is a further object of the invention to provide a minimally invasive surgical assembly which utilizes a 2 mm or smaller incision/port device.

It is also an object of the invention to provide a minimally invasive surgical assembly which will not scar a patient.

It is an additional object of the invention to provide a minimally invasive surgical assembly utilizing effective surgical instruments which are inserted into a 2 mm or smaller port device.

It is still another object of the invention to provide a minimally invasive surgical assembly with reduced number of parts.

In accord with these objects, which will be discussed in detail below, a minimally invasive surgical assembly according to the invention broadly includes an outer hollow needle which has an outer diameter of substantially 2 mm or smaller (the term "substantially", for purposes of this application meaning ±10%), and a coaxial surgical instrument having a shaft which extends through the outer hollow needle. The coaxial surgical instrument includes end effectors at the end of the shaft which are biased to an open position such that when the end effectors of the surgical instrument extend out of the needle they open, and they are closed by relative movement of the needle over them. The assembly preferably includes a first fixing element which is used to fix the relative location of the surgical instrument and the needle. The assembly also preferably includes a second fixing element which moves relative to the needle and is located on the outside thereof and which is used to fix the relative location of the needle to the patient. The second fixing assembly may include an anchoring element which permits the needle to be held at different angles relative to the patient.

According to one embodiment of the invention, the surgical instrument and needle are sized so that at least a portion of the shaft of the surgical instrument interferingly slides against the inner surface of the needle, thereby forming a seal which is effective against desufflation.

The surgical assembly of the invention may be used during laparoscopic surgery instead of using an extra trocar and laparoscopic instrument. In particular, with the surgical instrument (e.g., grasper) partially inserted in the needle (i.e., with the end effectors at least partially withdrawn inside the needle) and optionally locked relative to each other by the first fixing element, the needle is used to puncture the skin and advance into the body (e.g., the abdomen). At a desired location (typically under guidance of an already inserted scope), the movement of the needle is stopped. The surgical instrument is then unlocked (if previously locked) and advanced until the end effectors extend past the needle and spring open. The needle and surgical instrument may then further advanced until the end effectors extend over a structure in the body. Then, with the surgical instrument stationary, the needle is advanced relative to the surgical instrument to force the end effectors closed, thereby securely grasping the structure. The first fixing element may then be used to fix the needle relative to the surgical instrument to prevent release of the grasped structure. If desired, the needle with the surgical instrument fixed relative thereto and grasping the structure may be manipulated relative to the body wall (e.g., to lift, push, or otherwise move the structure). When the needle (or the grasped structure) is in a desired location in the body, the second fixing element is slid along the needle and into engagement with the skin of the patient, thereby fixing the grasping end effectors at a desired location in the body. At any time, the grasped structure can be released by causing the first fixing element to release the surgical instrument and then moving the needle backward relative to the surgical instrument, thereby permitting the end effectors to reopen. The surgical assembly can be pulled out of the body (preferably with the surgical instrument first moved backward relative to the needle to retract and close the end effectors and locate them inside the needle) leaving just a small puncture mark which will often heal without a scar.

The surgical assembly of the invention thereby accomplishes the objects of the invention with a minimum number of parts and may be used to replace expensive trocar assemblies and laparoscopic instruments.

Additional objects and advantages of the invention will become apparent to those skilled in the art upon reference to the detailed description taken in conjunction with the provided figures.

BRIEF DESCRIPTION OF THE DRAWINGS

FIGS. 3A-3E are broken representations of five different fixing element systems for fixing the shaft of surgical instrument relative to the needle.

FIG. 4 is a representation of a first embodiment of an anchoring element for fixing the location of the surgical assembly relative to the patient.

FIGS. 5A and 5B are respective top and side views of another embodiment of an anchoring element for fixing the location of the surgical assembly relative to the patient.

FIGS. 7A-7G are representations of seven different end effectors for the surgical instrument of the invention.

DETAILED DESCRIPTION OF THE PREFERRED EMBODIMENTS

Figure 1:
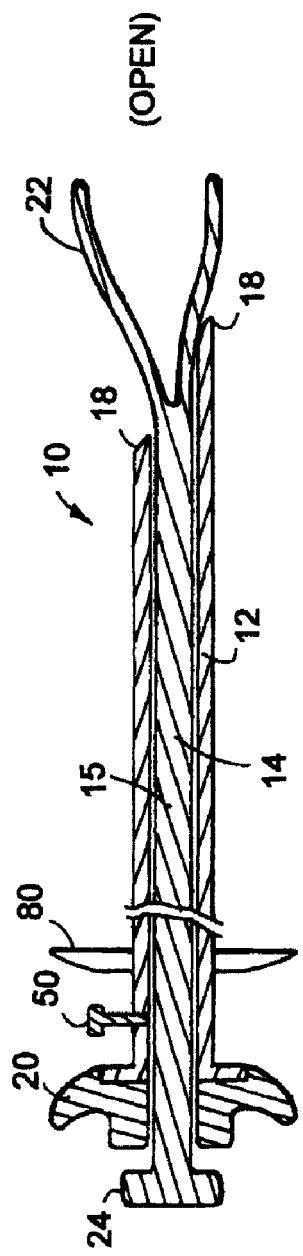
FIG. 1 is an enlarged broken cross sectional view of a first embodiment of the surgical assembly of the invention with the end effectors of the surgical instrument in an open (advanced) position.
Figure 2:
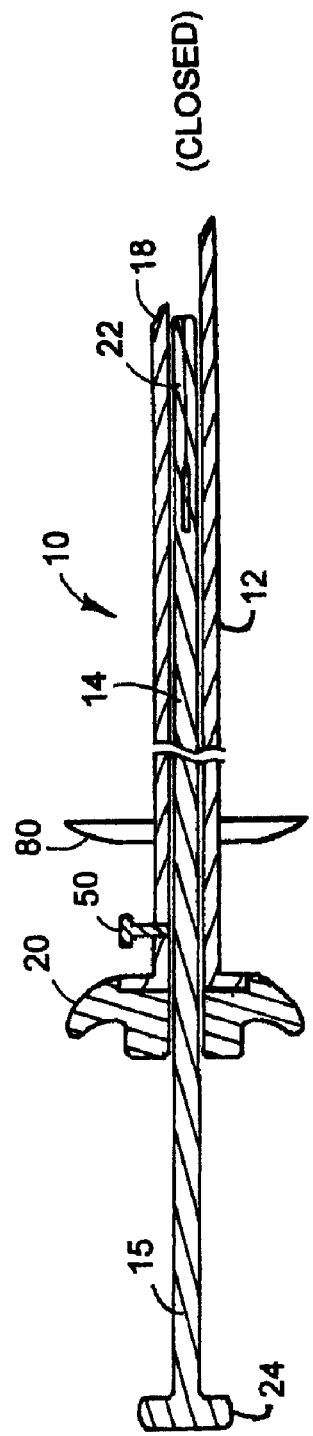
FIG. 2 is an enlarged broken cross sectional view of a first embodiment of the surgical assembly of the invention with the end effectors of the surgical instrument in a closed (retracted) position.

A minimally invasive surgical assembly 10 according to the invention and as seen in FIGS. 1 and 2 broadly includes an outer hollow needle 12 which has an outer diameter of substantially 2 mm (0.008 inches) or smaller, and a coaxial surgical instrument 14 having a shaft 15 which extends through the outer hollow needle. The needle 12 has a sharpened distal end 18 which is angled at about 35° relative to a longitudinal axis of the needle, and a proximal end having a knob or handle 20 for holding and manipulation of the needle. The inside diameter of the needle is approximately 1.5 mm (0.006 inches) and the wall thickness of the needle is approximately 0.25 mm (0.001 inch). The needle is typically between 10 and 30 cm long, and more typically between 13 and 18 cm long (although other sizes could be used, depending upon the surgery involved, and typically larger for obese patients and smaller for infants and small children), and is preferably made from stainless steel, although other materials could be utilized.

The coaxial surgical instrument 14 shown in FIGS. 1 and 2 is a grasper type instrument and includes end effectors 22 at the distal end of the shaft 15 and a handle or knob 24 at the proximal end of the shaft. The end effectors 22 are formed so that they biased to an open position as seen in FIG. 1, such that when the end effectors 22 of the surgical instrument 14 extend out of the needle 12 they open, and when the needle extends over them as in FIG. 2, they close. The end effectors 22 may be formed from the end of the shaft 15 as described in U.S. Pat. No. 6,616,683 to Toth et al. which is hereby incorporated by reference herein in its entirety, or in any other desired manner such as by forming end effectors and connecting them to the shaft. The shaft 15 of the surgical instrument 14 must be long enough to permit the end effectors to extend out of the needle as seen in FIG. 1. The surgical instrument 14 is preferably made from stainless steel, although other materials could be utilized for all or part of the instrument 14.

According to one aspect of the preferred embodiment of the invention, the surgical instrument 14 and needle 12 are sized so that at least a portion of the shaft 15 of the surgical instrument 14 interferingly slides against the inner surface of the needle 12, thereby forming a seal which is effective against desufflation. Thus, the outer diameter of the shaft 15 is approximately 1.49 mm (0.0059 inches), or about 0.01 mm smaller than the inner diameter of the needle. This small difference in diameters results in a sliding interference fit which can be felt as a drag and which effectively acts as a seal against desufflation. If desired, only a portion of the shaft be sized to interferingly slide against the inner surface of the needle. Alternatively, the needle may include an internal gasket or seal which seals against the outer diameter of the shaft.

Figure 3A:
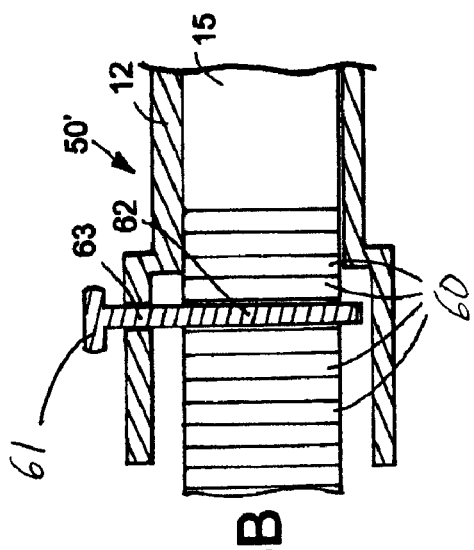

Turning to FIGS. 3A-3E, according to the preferred embodiment, the assembly 10 of the invention includes a first fixing mechanism, element, or system which is used to fix the relative location of the surgical instrument 14 and the needle 12. In FIG. 3A, the a first fixing system 50 is shown to include notches 52 on the shaft 15 of the surgical instrument 14, and a screw 54 which extends through a threaded radial hole 55 in the needle 12 or its handle. When it is desired to fix the surgical instrument 14 relative to the needle 12, the screw 54 is screwed (typically clockwise) into the needle and into engagement with a notch 52. When it is desired to release the surgical instrument 14, the screw 54 is unscrewed so that it is no longer engaged in the notch. It will be appreciated that instead of a screw 54 and a threaded radial hole 55, a spring loaded pin which extends through a radial hole in the needle (or needle handle) could be utilized to lock the surgical instrument 14 relative to the needle 12.

Figure 3B:
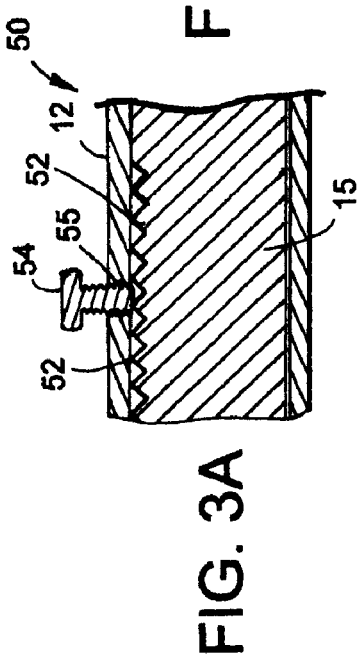

In FIG. 3B, a second fixing system 50' is shown to include radial grooves 60 on the shaft 15 of the surgical instrument and a clip 61 having spring arms 62 (one shown), and a shaft 63. The shaft 63 of the clip 61 extends through a wall of the needle or, more preferably, its handle, and the spring arms 62 engage a radial groove 60 on the shaft 15. When the shaft 15 of the needle is pushed or pulled relative to the needle, the spring arms 62 spread to permit movement of the shaft 15 past the clip 61. It will be appreciated that if the spring arms 62 are sufficiently springy, grooves are not required on the shaft 15 of the needle as the spring arms 62 will firmly hold the shaft in position.

Figure 3C:
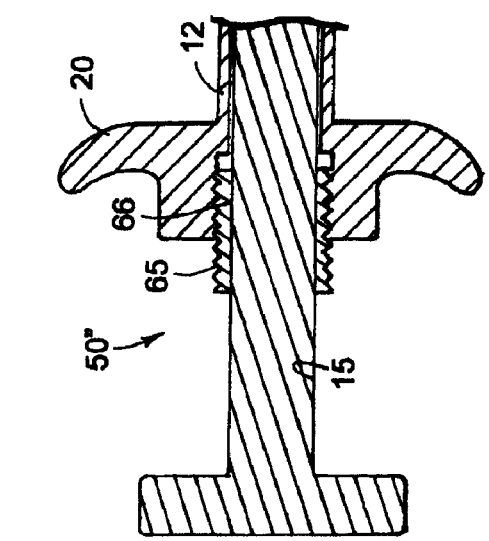

A third fixing system 50" is seen in FIG. 3C and includes a plastic screw 65 which extends around the shaft 15 of the surgical instrument 14, and an inner thread 66 located on the handle or knob 20 of the needle 12. When it is desired to fix the surgical instrument 14 relative to the needle 12, the screw 65 is screwed into the threaded handle or knob needle 20 of the needle 12. The plastic screw 65 and the inner thread 66 of the handle or knob 20 of the needle are sized to cause the plastic screw 65 to deform and tighten around the shaft 15 when the screw 65 is screwed into the thread 66, thereby fixing the locations of the needle 12 and surgical instrument 14 relative to each other. When it is desired to release the surgical instrument 14, the screw 65 is unscrewed sufficiently to permit movement of the surgical instrument relative to the needle. As will be appreciated by those skilled in the art, the screw 65 may have a gripping member such as a head (not shown) to help the practitioner apply torque.

Figure 3D:
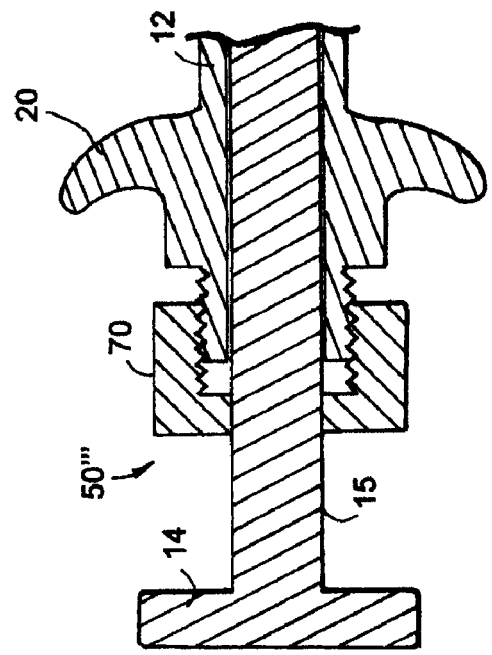

FIG. 3D shows a fourth fixing system 50''' which includes a thumb screw 70 and a handle portion 20 of the needle 12 which includes a thread (not shown), and which is flexible or plastic. In particular, the thumb screw 70 when screwed onto the handle portion threads causes the handle portion to clamp down on the shaft 15 of the surgical instrument 14 and lock the surgical instrument relative to the needle.

A fifth fixing system 50'''' is seen in FIG. 3E where a cam element 72 is rotatingly coupled to the needle handle 20' by a pin 73. When in a first orientation, the cam element 72 permits a rear portion 15' of the shaft 15 of the surgical instrument 14 to move in an uninhibited manner. When in a second orientation as shown in FIG. 3E, the cam element 72 engages the rear portion 15' of the shaft 15 and holds it fixed relative to the needle handle 20' and needle 12. It will be appreciated that in addition to the fixing system 50'''' which is different the fixing systems of FIGS. 3A-3D, the needle handle 20' and surgical instrument handle 24' are modified relative to the handles 20, 24 shown in FIGS. 1 and 2 and FIGS. 3A-3D.

The assembly also preferably includes a second fixing element which moves relative to the needle and is located on the outside thereof and which is used to fix the relative location of the needle to the patient. More particularly, as seen in FIG. 4, the second fixing element is a soft plastic suction cup 80 which engages and is frictionally slidable over the outer surface of the needle 12, and which can be pressed against the abdominal wall of a patient to cause a suction connection. If desired, the outer surface of the needle 12 may be provided with mating elements such as bumps, serrations, or grooves (not shown), and the suction cup 80 may be provided with a reciprocal mating element (not shown) for engaging the mating element of the outer surface of the needle 12 to more strongly fix the location of the suction cup 80 relative to the needle 12.

Turning to FIGS. 5A and 5B, a second embodiment of the second fixing assembly is seen to include a plastic suction cup 80' having a top proximal hole 82 and a plurality of bayonet-type grooves 84 through which the needle 12 can be maneuvered. The suction cup 80' thereby permits the needle 12 to be held at different angles relative to the patient.

Figure 6:
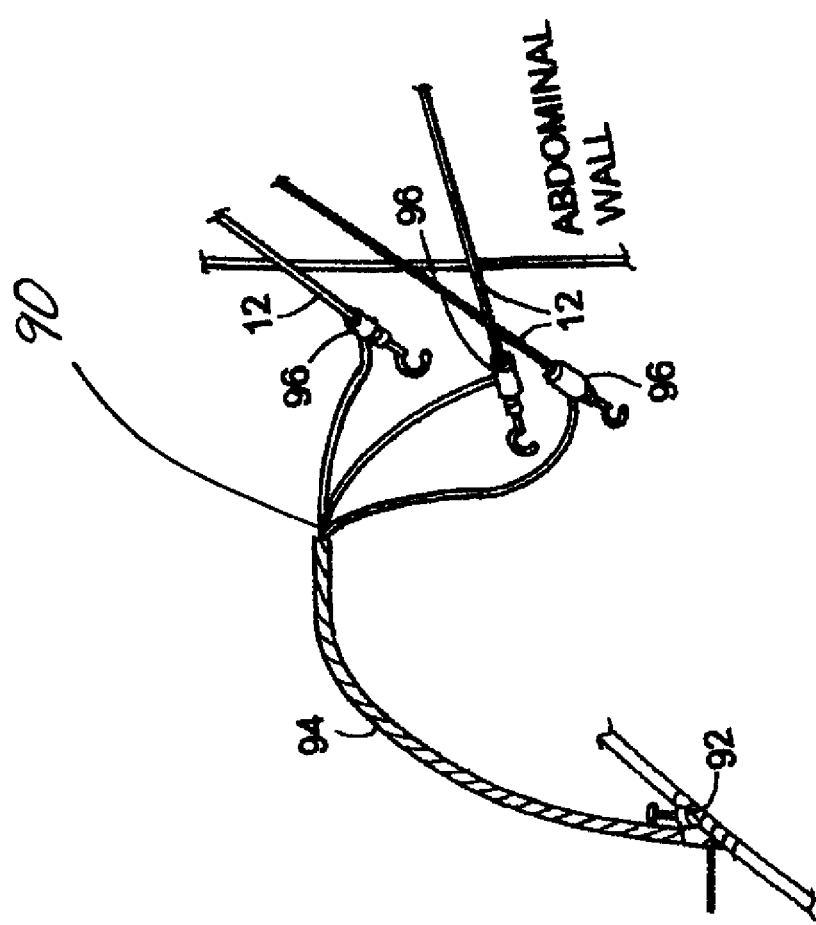
FIG. 6 is a schematic view of another mechanism fixing the location of the surgical assembly relative to the patient.

In lieu of a suction cup, it is possible to fix the location of the needle 12 and surgical instrument 14 relative to the patient by using standard equipment and modifying the surgical assembly of the invention slightly. Thus, as seen in FIG. 6, a standard multiheaded clip 90 is provided which is fixed by a clamp 92 to the side of an operating room table. The multiheaded clip 90 includes a malleable metal rod 94 and a plurality of clip elements 96. The surgical assembly 10 may then be held in a desired position relative to the patient by providing the needle 12 or surgical instrument 14 with a clip receiver or groove which may be located on the outside surface of the needle handle or on the handle or knob of needle or surgical instrument.

Figure 7A:
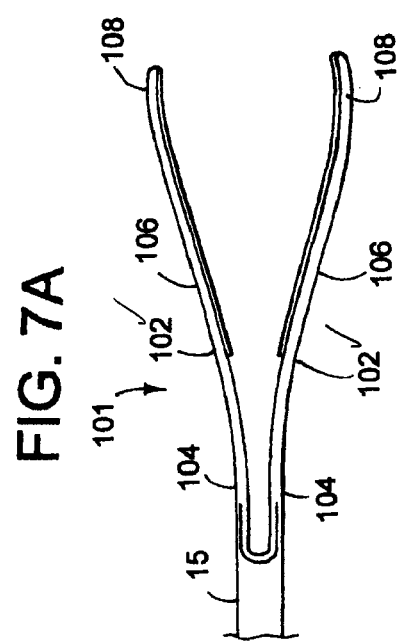

As will be appreciated by those skilled in the art, the surgical instrument 14 of the invention may take various forms. Thus, FIGS. 7A-7G show representations of seven different end effectors for the surgical instrument of the invention (although others could be utilized). FIG. 7A shows a detailed view of a grasper such as seen in FIGS. 1 and 2. The grasper end effectors 101 include two arms 102 which extend from shaft 15, each of which is approximately 19 mm (0.75 inch) long. The arms are slightly rounded on their outer peripheries in the same profile as the shaft 15, with each rounded surface forming an arc of between forty-five and ninety degrees. The first portions 104 (e.g., about 4 mm) of the arms are relatively straight in their at rest open position. The middle portions 106 of the arms 102 then angle away from each other (each at between 6° and 18°, and most preferably at about 12° from the horizontal) until they extend approximately 7 mm apart from each other. In order to provide a good spring load, the middle portions of the arms may be reinforced with or formed from spring steel. The tips 108 (e.g., approximately 3 mm) of the arms are then bent back to parallel the first portions 104. Their outer surfaces may also be flattened.

If desired, the grasper of FIG. 7A can be formed from a solid rod or a tube of steel, by cutting the end of the tube in half to form arms (e.g., via use of a laser or an EDM machine), further removing material from the underside of each arm at the first portions 104, and then bending the arms at the intersections of the first portions 104 and middle portions 106, and at the intersections of the middle portions 106 and tips 108.

Figure 7B:
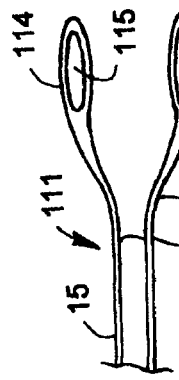

FIG. 7B is a representation of lung clamp end effectors 111. The lung clamp end effectors extend from the shaft 15 with arms 112 which terminate in loops 114 which define openings 115. While not shown in detail in FIG. 7B, the arms 112 are similar to the arms of the grasper of FIG. 7A in that they are slightly rounded on their outer peripheries in the same profile as the shaft 15, include first portions 116 which are relatively straight in their at rest open position and middle portions 118 which angle away from each other until they extend approximately 6 mm apart from each other. The loops 114 are then bent back to parallel the first portions 116. In order to provide a good spring load, the middle portions of the arms may be reinforced with or formed from spring steel.

Figure 7C:
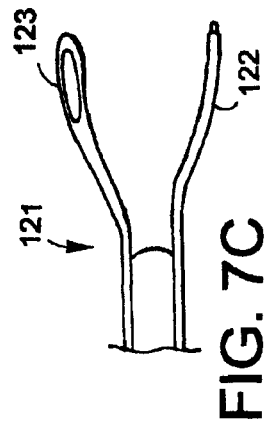

FIG. 7C is a representation of hybrid end effectors 121 including one grasper 122 and one lung clamp 123. The grasper 122 is substantially as described above with reference to FIG. 7A, and the lung clamp 123 is substantially as described above with reference to FIG. 7B.

Figure 7D:
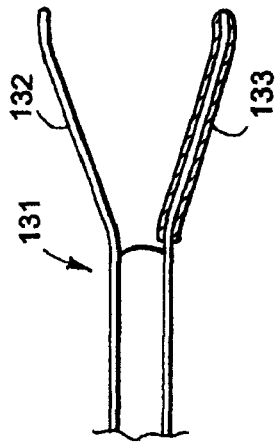

FIG. 7D is a representation of non-crushing clamping end effectors 131 including one grasper 132 and a rubber covered arm 133.

Figure 7E:
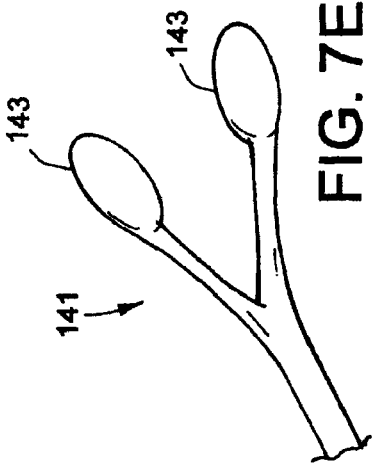

FIG. 7E is a representation of retractor end effectors 141. The retractor end effectors 141 are formed from wire mesh elements 143 which at rest are substantially flat, but which are bent into an arcuate shape when retracted into the needle.

FIG. 7F is a representation of a grasper similar to that of FIG. 7A. The primary differences between the grasper end effectors 151 of FIG. 7F and the grasper end effectors 101 of FIG. 7A are that the arms 152 are each approximately 25 mm (1 inch) long, the middle portions 156 angle away from each other (at about 50° or 250 from the horizontal) until they extend approximately 10 mm apart from each other, and the tip portions 158 are approximately 12 mm long and bend back slightly beyond being parallel to the first portions 154 so that they are angled slightly toward each other.

FIG. 7G is a representation of a crushing grasper 161 shown in a closed position within a needle 12. The crushing grasper 161 is similar to the grasper 101 of FIG. 7A except that it is slightly longer (approximately 22 mm long), and the tip portions 168 have teeth 169a and have a rounded front 169b such that they present a blunt almost hemispherical surface. When the end effectors 161 of FIG. 7G are moved forward relative to the needle 12, they preferably remain in a closed position until approximately half the length of the arms 162 extend beyond the needle. Thus, as will be discussed below, the end effectors of the surgical instrument 14 may act as an obturator relative to the needle to guard the needle from causing accidental needle tip trauma.

Figure 10A:
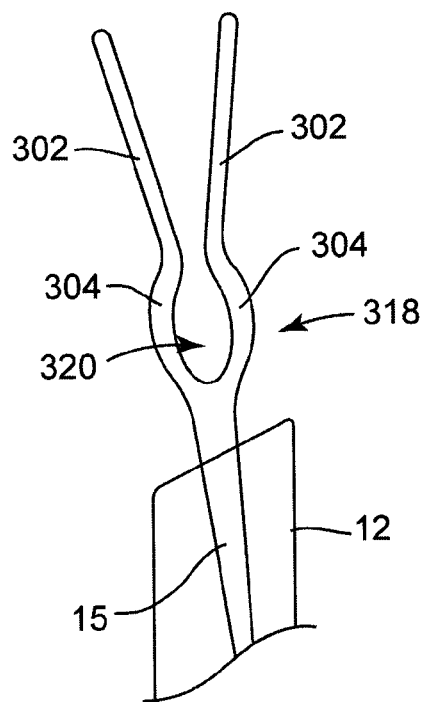
FIGS. 10A-10C are schematic representations of a surgical instrument in various relative longitudinal positions relative to an outer needle and having end effectors according to another embodiment of the present invention.
Figure 10B:
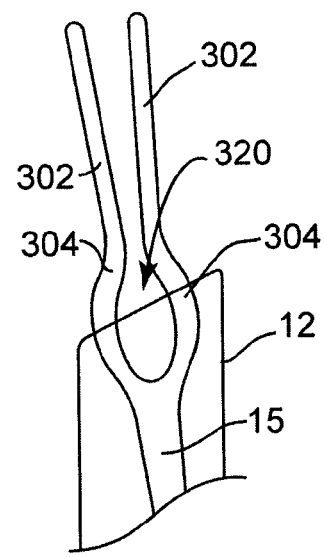
Figure 10C:
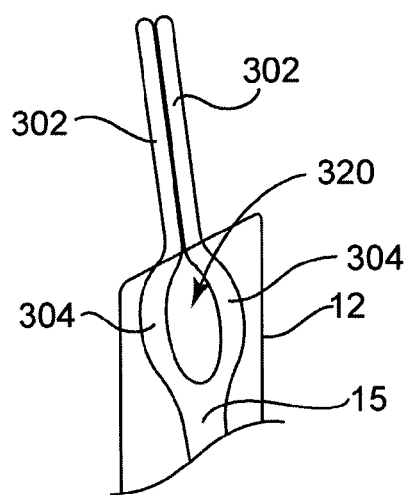

Referring now to FIGS. 10A-10C, schematically depicted is a surgical instrument in various relative longitudinal positions relative to an outer needle 12 and having end effectors that include a bulge or protuberance 318 forming an interior cavity 320, according to an alternative embodiment of the present invention. More specifically, as shown, the end effectors comprise (i) a distal portion including jaw members 302 that are operative in grasping, and (ii) a portion coupled to the end of shaft 15 and having laterally protruding members 304 forming interior cavity 320 therebetween. As will be understood by those skilled in the art, in various uses of the surgical instrument, cavity 320 allows for positioning therein a portion of tissue that extends through jaw members 302, thus, for example, providing for more secure grasping of the tissue and/or facilitating closure of the jaws (e.g., preventing the tissue from obstructing or jamming closure of the jaws).

In FIG. 10A, the surgical instrument is disposed such that the jaw members 302 and the protruding members 304 are external to the needle, with the jaw members in an open position due to the elastic bias (i.e., which is relaxed in the open position). In FIG. 10B, the surgical instrument is disposed such that the jaw members 302 are external to the needle and the protruding members 304 are partially retracted within the needle, causing the jaw members 302 to partially close based on the mechanical bias configuration provided in this implementation. In FIG. 10C, the surgical instrument is disposed such that the jaw members 302 are external to the needle and the protruding members 304 are fully retracted within the needle, causing the jaw members 302 to completely close (e.g., their inner surfaces contact each other) based on the mechanical bias configuration provided in this implementation. In some embodiments, retraction of the protruding portion into the needle may laterally compress the protruding members 304 (e.g., in some embodiments, the lateral extent of the protruding members when external to the needle may be greater than the inner diameter of the needle), thus decreasing the lateral dimension of the cavity to some extent.

As may be appreciated, the mechanical biasing (e.g., longitudinal strain distribution) and/or the dimensioning of the protruding portions relative to the needle diameter may be varied to provide different rates of jaw closing with respect to the relative longitudinal position of the surgical instrument and the outer needle. For instance, in some implementations, the mechanical bias or strain distribution and/or the dimensions of the protruding portion relative to the needle inner diameter may be designed such at the jaws remain entirely open until the needle extends over the jaws.

It will also be understood that in various alternative implementations, only one of the end effectors may include a protuberance to provide the interior cavity portion. It may also be appreciated that while in the embodiment of FIG. 10A-C, the laterally protruding portions are entirely separated from each other along the cavity region such that there is access to the interior cavity from a direction substantially perpendicular to the lateral and longitudinal directions, in various alternative embodiments the laterally protruding portion may partially or entirely enclose the interior cavity azimuthally relative to the longitudinal axis. For instance, in some embodiments the laterally protruding portions may extend continuously and coextensively (e.g., integrally formed) in the azimuthal direction about the longitudinal axis, thus forming a mouth-like structure comprising a closed cavity that is accessible only through the opening formed through the jaw members when the jaw members are in an open position.

The surgical assemblies of the invention may be used during laparoscopic surgery instead of using extra trocars and laparoscopic instruments. In particular, with the surgical instrument 14 (e.g., grasper end effectors 111) partially inserted in the needle 12 (i.e., with the end effectors withdrawn at least partially inside the needle) and optionally locked relative to each other by the first fixing element (e.g., fixing system 50), the needle 12 is used to puncture the skin and advance into the body (e.g., the abdomen). At a desired location (typically under guidance of an already inserted scope), the movement of the needle is stopped. The surgical instrument 14 is then unlocked (if previously locked) and advanced until the end effectors 111 extend past the needle 12 and spring open. The needle and surgical instrument may then further advanced until the end effectors extend over a structure in the body. Then, with the surgical instrument stationary, the needle is advanced relative to the surgical instrument to force the end effectors 111 closed, thereby securely grasping the structure. The first fixing element or system (e.g., system 50) may then be used to fix the needle relative to the surgical instrument to prevent release of the grasped structure. If desired, the needle with the surgical instrument fixed relative thereto and grasping the structure may be manipulated relative to the body wall (e.g., to lift, push, or otherwise move the structure). When the needle (or the grasped structure) is in a desired location in the body, the second fixing element (e.g., 80) is slid along the needle and into engagement with the skin of the patient, thereby fixing the grasping end effectors at a desired location in the body. At any time, the grasped structure can be released by causing the first fixing element to release the surgical instrument and then moving the needle backward relative to the surgical instrument, thereby permitting the end effectors to reopen. The surgical assembly can be pulled out of the body (preferably with the surgical instrument first moved backward at least partially relative to the needle to retract and close the end effectors) leaving just a small puncture mark which will often heal without a scar.

It is noted that because of the small diameter of the surgical assembly, withdrawal of the needle assembly from the abdomen will not cause desufflation, and should not require stitching to close the wound. It is also noted that because of the small diameter of the surgical assembly the elimination of a trocar port, the surgical assembly can be easily moved in any direction (i.e., it can be easily angled) during surgery. Those skilled in the art will understand that although the outer diameter of the needle in the illustrative embodiment described hereinabove is 2 mm, in various alternative embodiments the needle outer diameter may be larger than 2 mm (e.g., 2.5 mm or 3 mm, etc.) while still producing a wound that does not require stitching to close, and which wound may often heal without a scar.

The surgical assembly of the invention thereby accomplishes the objects of the invention with a minimum number of parts and may be used to replace expensive trocar assemblies and laparoscopic instruments.

Figure 8A:
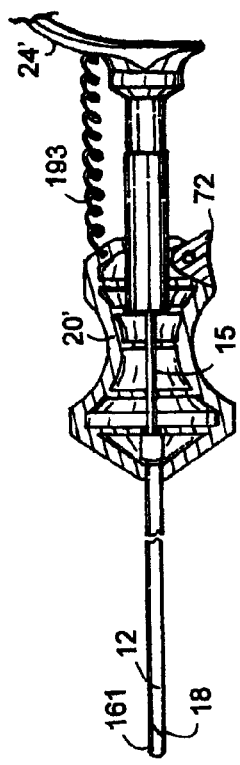
FIG. 8A-8D are representations of a modified surgical instrument having end effectors acting as an obturator, and with the end effectors located in a-rest shielding position, a puncturing position, an extended position, and a withdrawn position respectively.
Figure 8B:
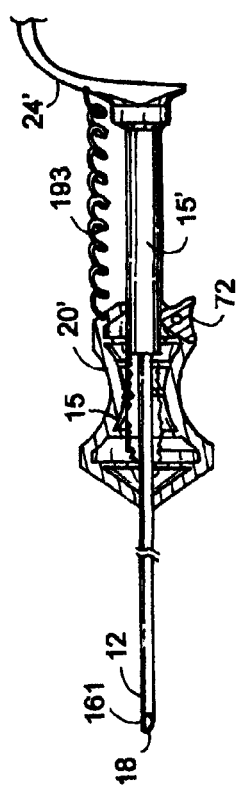
Figure 8C:
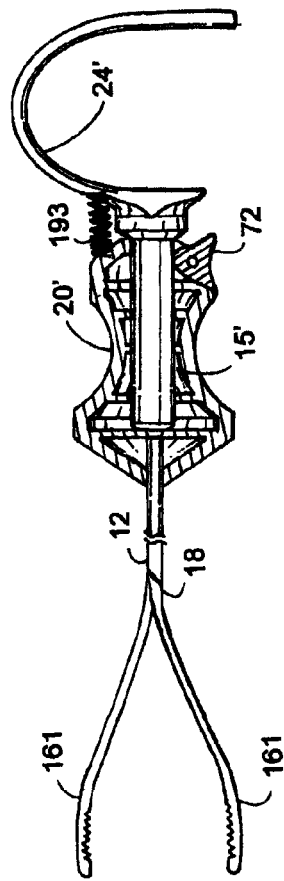
Figure 8D:
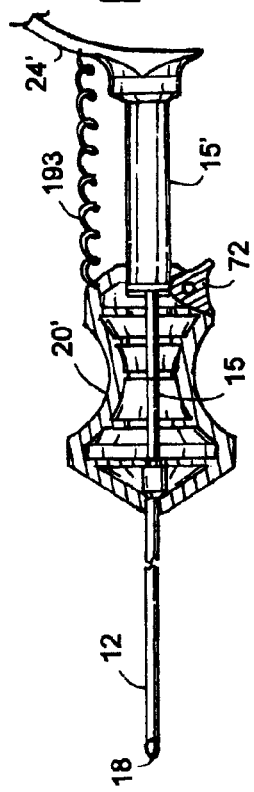

According to another aspect of the invention, as previously mentioned, the tips of the end effectors of the surgical instrument may be used to function as an obturator. Thus, as seen in FIGS. 8A-8D, a surgical assembly combining aspects seen in FIGS. 3E and 7G is shown, except that a spring 193 is provided and coupled to the handles 20', 24' of the needle and surgical instrument respectively. Spring 193, in an at rest position, causes the rounded end effectors 161 to assume a position where the end effectors extend out of the needle 12 but remain in a closed position as seen in FIG. 8A. In this partially extended position, the end effectors 161 act as an obturator or protection from accidental needle tip trauma. When the surgical assembly is used to puncture skin as seen in FIG. 8B, pressure is placed on the end effectors, thereby causing the end effectors 161 to be pushed back into and thereby exposing the needle, and causing the surgical instrument to move backward relative to the needle, thereby placing spring 193 under tension. When the skin is punctured and the needle extends into a cavity and pressure on the end effectors is released, the spring 193 pushes the surgical instrument forward to reassume the position of FIG. 8A. When it is desired to extend the end effectors 161 to grasp a structure, the surgical instrument may be pushed forward relative to the needle as seen in FIG. 8C, thereby placing the spring 193 under compression, and opening the end effectors 161. The end effectors may then be closed over the object by pulling end effectors backward relative to the needle whereby the needle acts on the end effectors to at least partially close them, with the spring 193 assuming a partially compressed position. The grasping position (and any other position) may be locked at any time using the fixing element (e.g., cam 72). If it is desired to pull the end effectors totally into the needle as seen in FIG. 8D, that may be accomplished by pulling the surgical instrument backward relative to the needle, again placing the spring 193 in tension. The surgical instrument can be locked in that position using the fixing element.

Figure 9A:
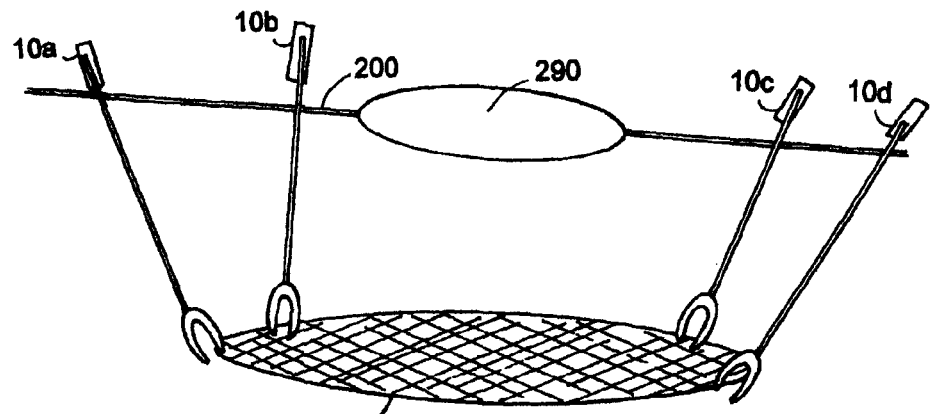
FIGS. 9A-9D are schematic diagrams showing the use of four surgical assemblies of the invention being used for a hernia repair operation.
Figure 9B:
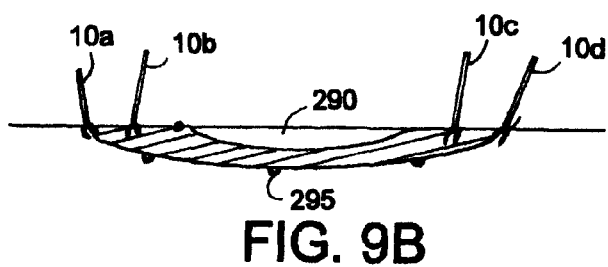
Figure 9C:
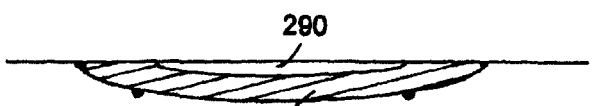
Figure 9D:
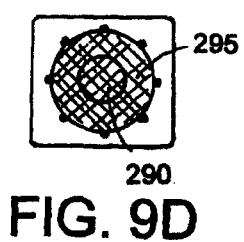

Use of a plurality of surgical assemblies 10a-10d is seen in FIGS. 9A-9D with respect to a hernia repair operation. In particular, an abdominal wall 200 is seen with a hernia (opening) 290. The hernia 290 is to be repaired with mesh 290 which has been inserted into the abdomen under guidance of a laparoscope (not shown). As seen in FIG. 9A, four surgical assemblies 10a-10d according to the invention have been used to pierce the abdominal wall. The four assemblies 10a-10d are then used to grasp corner areas of the mesh 295 by moving the grasper end effectors out of their respective needles and over and around the mesh corners, and by moving the needles forward relative to the grasper instruments to force the end effectors closed over the mesh. The needles and surgical instruments are then preferably locked relative to each other (using first fixing mechanisms or systems such as discussed above with reference to FIGS. 3A-3E), and the assemblies 10a-10d are pulled upward to cause the mesh 295 to lie directly below the hernia 290 as seen in FIG. 9B. The assemblies are then preferably locked in place relative to the abdominal wall using mechanisms such as discussed above with reference to FIGS. 4, 5A, 5B, and 6. Then, using a laparoscopic stapler (not shown) typically introduced through a standard trocar port, the mesh is stapled in place. The mesh may then be released by the assemblies 10a-10d by unlocking the surgical instruments, unlocking the second fixing mechanisms, and moving the respective needles backward in order to open the end effectors. After the mesh is released, the end effectors of the surgical instruments are withdrawn at least partially into the needles (and optionally locked in place), and withdrawn from the abdomen, leaving the mesh 295 stapled in place as seen in FIGS. 9C and 9D.

It will be appreciated by those skilled in the art that the minimally invasive surgical assemblies of the invention can be used for various other surgical procedures, including but not limited to tuboplasty, gastric bypass, bowel connection, kidney surgery, appendectomy, menisectomy, discectomy, etc. The minimally invasive surgical assemblies of the invention also have particularly advantageous use in neonatal and pediatric surgeries.

There have been described and illustrated herein several embodiments of a minimally invasive surgical assembly and methods for the use thereof. While particular embodiments of the invention have been described, it is not intended that the invention be limited thereto, as it is intended that the invention be as broad in scope as the art will allow and that the specification be read likewise. Thus, while particular materials for making the needle and surgical instrument have been disclosed, it will be appreciated that other materials may be used as well. In addition, while particular fixing elements and systems have been disclosed for fixing the surgical instrument relative to the needle, it will be understood that other mechanisms can be used. For example, and not by way of limitation, a latch-catch system can be used. Also, while particular fixing elements and systems for fixing the location of the surgical assembly relative to the patient have been described, it will be recognized that other mechanisms can be used for that as well. Furthermore, while particular end effectors such as graspers, lung clamps, etc., have been described for the surgical instrument, it will be understood that instruments with different end effectors such as (but not limited to) dissectors, staplers, scissors, suction/irrigators, clamps, biopsy forceps, etc., an be similarly used. Also, the arms of the end effectors need not be of equal length. Further, while the surgical instrument and needle have been shown as being straight, because of their small diameter they may be bent together by the user, or one or both may be formed with a bend (arc). Moreover, while particular configurations have been disclosed in reference to the handles of the surgical instrument and the needle have been disclosed, it will be appreciated that other configurations could be used as well. In addition, while the needle was described as being a particular size and having a sharp end with a certain angle, it will be appreciated that other size needles can be used and the sharp can be at different angles. It will therefore be appreciated by those skilled in the art that yet other modifications could be made to the provided invention without deviating from its spirit and scope as claimed.

What is claimed is:

1. A surgical method, comprising:
    obtaining a surgical assembly having (i) a hollow needle with a sharp distal end, and (ii) a surgical instrument having a shaft that extends through said hollow needle, said surgical instrument being movable relative to said hollow needle and including at an end of said shaft first and second end effectors that are biased toward an open position;
    with said first and second end effectors in a closed position inside said hollow needle wherein said first and second end effectors contact one another, using said sharp distal end of said hollow needle to puncture skin of a patient at an operative site and insert a distal portion of said surgical assembly into a cavity of said patient;
    moving said surgical instrument forward relative to said needle to cause said first and second end effectors to extend out of said needle and to automatically open relative to each other;
    moving said end effectors over an object in the cavity; and
    moving said needle forward relative to said surgical instrument to cause the sharp distal end of the hollow needle to directly contact both said first and second end effectors during forward movement of the needle relative to the first and second end effectors in order to close the first and second end effectors over said object.

2. The surgical method according to claim 1, further comprising:
    withdrawing said surgical assembly from said patient through the operative site formed in the skin of the patient upon inserting the surgical assembly into the patient, and allowing the operative site to heal independently of stitching.

3. The surgical method according to claim 2, wherein an outer diameter of the hollow needle is substantially 2 mm or smaller.

4. The surgical method according to claim 1, further comprising pushing or pulling the object by moving said needle and said surgical instrument together.

5. The surgical method according to claim 1, further comprising releasing said object by moving said needle backward relative to said surgical instrument to permit said first and second end effectors to automatically open relative to each other.

6. The surgical method according to claim 1, wherein an outer diameter of the hollow needle is substantially 2 mm or smaller.

7. The surgical method according to claim 1, wherein said hollow needle has an inner surface and said shaft has an outer surface, and said outer surface and said inner surface are sized so that at least a portion of said shaft interferingly slides against said inner surface of said needle, thereby forming a seal which is effective against desufflation.

8. The surgical method according to claim 1, wherein said surgical assembly further comprises a first fixing means coupled to said surgical instrument and said needle for fixing a relative location of said surgical instrument relative to said needle.

9. The surgical method according to claim 8, wherein said surgical assembly further comprises a second fixing means coupled to and movable relative to said needle for fixing a relative location of said needle to the patient.

10. The surgical method according to claim 1, wherein:
    said first and second end effectors each comprise a respective first portion and a respective second portion;
    wherein at least one of the respective first portions protrudes laterally relative to a longitudinal axis of said shaft such that the respective first portions form a cavity therebetween when the first and second end effectors are in the closed position; and
    wherein the respective second portions extend distally from the respective first portions in a parallel configuration relative to the longitudinal axis of the shaft and contact one another along respective surfaces when the first and second end effectors are in the closed position.

11. The surgical method according to claim 10, wherein each of the first portions protrudes laterally relative to the longitudinal axis.

12. The surgical method according to claim 1, wherein:
    an outer diameter of the sharp distal tip of the hollow needle is dimensioned such that a wound formed from the hollow needle puncturing the skin of said patient is capable of being closed independent of stitching.

13. The surgical method according to claim 1, wherein:
    the sharp distal end of the hollow needle has an outer surface and an inner surface, the outer surface contacts the skin of the patient during puncture of the skin of the patient, and the inner surface directly contacts both the first and second end effectors during forward movement of the needle relative to the end effectors to cause the first and second end effectors to close over the object.

14. The surgical method according to claim 1, wherein the first and second end effectors are configured such that direct contact between the sharp distal end of the hollow needle and both said first and second end effectors causes the first and second end effectors to directly contact one another while disposed distally relative to the sharp distal end of said hollow needle.

15. The surgical method according to claim 14, wherein the first and second end effectors each have elongate surfaces that are configured to directly contact one another while disposed distally relative to the sharp distal end of said hollow needle.

* * * * *